(12) United States Patent
Leussler et al.

(10) Patent No.: US 12,099,103 B2
(45) Date of Patent: Sep. 24, 2024

(54) RADIO FREQUENCY HEAD COIL WITH RESPIRATORY MASK

(71) Applicant: KONINKLIJKE PHILIPS N.V., Eindhoven (NL)

(72) Inventors: Christoph Gunther Leussler, Hamburg (DE); Michael Gunter Helle, Hamburg (DE); Daniel Wirtz, Hamburg (DE); Gereon Vogtmeier, Hamburg (DE); Steffen Weiss, Hamburg (DE); Sunil Kumar Vuppala, Bangalore (IN); Rajendra Singh Sisodia, Bangalore (IN)

(73) Assignee: Koninklijke Philips N.V., Eindhoven (NL)

( * ) Notice: Subject to any disclaimer, the term of this patent is extended or adjusted under 35 U.S.C. 154(b) by 304 days.

(21) Appl. No.: 17/632,244

(22) PCT Filed: Aug. 7, 2020

(86) PCT No.: PCT/EP2020/072257
§ 371 (c)(1),
(2) Date: Feb. 2, 2022

(87) PCT Pub. No.: WO2021/028342
PCT Pub. Date: Feb. 18, 2021

(65) Prior Publication Data
US 2022/0291308 A1    Sep. 15, 2022

(30) Foreign Application Priority Data
Aug. 14, 2019 (EP) ..................................... 19191779

(51) Int. Cl.
*G01R 33/34* (2006.01)
*A61B 5/00* (2006.01)
(Continued)

(52) U.S. Cl.
CPC ...... *G01R 33/34084* (2013.01); *A61B 5/0036* (2018.08); *A61B 5/055* (2013.01); *A61M 16/06* (2013.01); *G01R 33/283* (2013.01)

(58) Field of Classification Search
CPC .. G01R 33/34046–34092; A61B 5/055; A61B 5/0036; A61M 16/06–0655; A61M 16/0683–0694
See application file for complete search history.

(56) References Cited

U.S. PATENT DOCUMENTS 5,435,302 A    7/1995 Lenkinski et al.
2009/0088627 A1    4/2009 Piferi et al.
(Continued)

FOREIGN PATENT DOCUMENTS

EP    2425781 A1    3/2012
JP    2006034310 A    2/2006
(Continued)

OTHER PUBLICATIONS

M Subrahmanyam, Safety Features in Anaesthesia Machine Indian J Anaesth. Sep.-Oct. 2013; 57(5): 472-480.
(Continued)

*Primary Examiner* — Carolyn A Pehlke

(57) ABSTRACT

Embodiments of the present application provide a radio frequency head coil (300), RE head coil. The RE head coil (300) comprises a coil former (310) comprising at least a first leg and a second leg arranged at a distance from each other to define a space there between, the coil former (310) being at least sectionally flexible and having at least one first fastening portion (315, 316) arranged adjacent to the space (314), and a respiratory mask (320) comprising a gas outlet (324) and at least one second fastening portion (322, 323), wherein in an operable condition in which the RE head coil (300) is adapted to be arranged at least in sections around a head of a patient (S) and in which the second fastening
(Continued)

portion (322, 323) is adapted to be fastened to the first fastening portion (315, 316), the gas outlet (324) is disposed within the space (314).

20 Claims, 2 Drawing Sheets

(51) Int. Cl.
*A61B 5/055* (2006.01)
*A61M 16/06* (2006.01)
*G01R 33/28* (2006.01)

(56) References Cited

U.S. PATENT DOCUMENTS

| | | |
|---|---|---|
| 2010/0329414 A1 | 12/2010 | Zhu et al. |
| 2014/0002086 A1 | 1/2014 | Gross et al. |
| 2014/0073908 A1 | 3/2014 | Biber |
| 2015/0196723 A1 | 7/2015 | Matusik |
| 2015/0231357 A1 | 8/2015 | Lu et al. |
| 2016/0187436 A1* | 6/2016 | Piron ............... G01R 33/34053 324/309 |
| 2019/0219648 A1 | 7/2019 | Lin et al. |
| 2021/0121066 A1* | 4/2021 | Rheineck ......... G01R 33/34007 |

FOREIGN PATENT DOCUMENTS

| | | | |
|---|---|---|---|
| JP | 2013034662 A | * | 2/2013 |
| JP | 2014073294 A | | 4/2014 |
| WO | 2012156866 A1 | | 11/2012 |

OTHER PUBLICATIONS

International Search Report and Written Opinion from PCT/EP2020/072257 mailed Feb. 18, 2021.

* cited by examiner

RADIO FREQUENCY HEAD COIL WITH RESPIRATORY MASK

CROSS REFERENCE TO RELATED APPLICATIONS

This application is a U.S. national phase application of International Application No. PCT/EP2020/072257 filed on Aug. 7, 2020, which claims the benefit of EP Application Serial No. 19191779.8 filed on Aug. 14, 2019 and is incorporated herein by reference.

FIELD OF THE INVENTION

The present invention relates to medical imaging, and relates in particular to a radio frequency head coil, RF head coil, and to a magnetic resonance imaging system, MRI system.

BACKGROUND OF THE INVENTION

In medical imaging, and in particular in magnetic resonance imaging, MRI, as an aim it may be considered to keep movements of a patient during image acquisition as small as possible or to avoid them as far as possible. Because, motion in images may cause blurriness, shadowing, or the like, which may sacrifice the clarity of the images, or, generally, the quality of images.

Accordingly, it may be attempted, for example, to fix a patient as immobile as possible, or to monitor his movement and perform imaging when the patient is not moving.

There are options for fixing a patient during image acquisition which have already been suggested. One example is US 2010/0329414 A1, in which the patient is maintained on a patient support table in a fixed position using an immobilization device that is provided as a molded head mask.

Further, in MRI, radio frequency coils, RF coils, may be used as receivers, and sometimes also as transmitters, of radiofrequency, RF, signals generated in MRI. Such an RF coil may, for example, complicate fixation of the patient or monitoring of his movements.

SUMMARY OF THE INVENTION

There may therefore be a need to improve magnetic resonance imaging, in particular in terms of improving a radio frequency head coil.

The object of the present invention is solved by the subject-matter of the independent claims, wherein further embodiments are incorporated in the dependent claims. It should be noted that the following described aspect of the invention equally applies to the radio frequency head coil, RF head coil, and to a magnetic resonance imaging system, MRI system, a LINAC system, an MR-PET system or an MR-HIFU system.

According to a first aspect, there is provided a radio frequency head coil, RF head coil. The RF head coil comprises:

a coil former comprising at least a first leg and a second leg arranged at a distance from each other to define a space there between, the coil former being at least sectionally flexible and having at least one first fastening portion arranged adjacent to the space; and a respiratory mask comprising a gas outlet and at least one second fastening portion;

wherein in an operable condition in which the RF head coil is adapted to be arranged at least in sections around a head of a patient and in which the second fastening portion is adapted to be fastened to the first fastening portion, the gas outlet is disposed within the space.

The RF head coil may particularly be provided as a so-called birdcage coil, or the like. In at least some embodiments, the RF head coil may be provided as an MM coil array having a plurality of channels, e.g. 8, 16, 32 or 64 channels. Further, the RF head coil may be configured as a receive-only coil or a transmit-and-receive coil. It may also be dedicated to a patient.

The space between the legs may also be referred to as an opening. The first fastening portion may be configured for a non-positive connection, a positive connection, a combined non-positive/positive connection and/or a material connection, and in particular for an adhesive connection, a mechanical connection, etc. between the RF head coil and the respiratory mask, wherein mechanical fasteners may preferably be made from a magnetic resonance compatible material.

The respiratory mask may be dedicated to a patient and adapted to cover either the nose or the mouth or to cover both the nose of a patient. The second fastening portion may be configured for a non-positive connection, a positive connection, a non-positive/positive connection and/or a material connection, and in particular for an adhesive connection, a mechanical connection, etc. between the RF head coil and the respiratory mask, wherein mechanical fasteners may preferably be made from a magnetic resonance compatible material.

An effect of this MM system may be that the RF head coil and the respiratory mask are combined to one assembly. Thus, the functionalities of an RF head coil and a respiratory mask can be combined in one assembly, simplifying, for example, a patient's setup for e.g. MRI.

According to an embodiment, the respiratory mask may comprise a mask body, dimensionally adapted to a patient's facial contour, and the at least one second fastening portion, disposed at the mask body and adapted to be attached to the at least one first fastening portion of coil former, wherein the gas outlet opens into an inner side of the mask body and is adapted to be connected to a gas supply.

The mask body may provide a seal to allow an airtight seat on the patient's face. The second fastening portion may provide a releasable connection to the RF head coil, and in particular to the coil former or the first fastening portion, so that the respiratory mask may be released as needed and cleaned or replaced separately.

In an embodiment, the respiratory mask may selected from: a CPAP (continuous positive airway pressure) mask, a sedation mask preferably adapted to supply a gaseous sedative, etc.

For example, oxygen, the sedative or other medical gases may be supplied from the gas supply via the gas outlet of the mask to the patient's respiratory system. In this context, inhalation sedation may be regarded as a form of conscious sedation where an inhalable drug is administered. The gas supply may be provided as an external device, which may be controlled remotely or autonomously. When, for example, the sedation mask is selected, the patient may be sedated during imaging, thereby reducing Mill scan time by using the combination of sedation mask and RF head coil which allows sedation adherence during the Mill scan. This may allow to obtain diagnostic images of high quality. by sedating the patient and thereby preventing movement of the patient. In this way, motion in pictures, which can cause blurriness and shadowing, which sacrifices the clarity of the photographs, may be prevented.

According to an embodiment, the respiratory mask may be manufactured by additive manufacturing.

For example, a 3D (three-dimensional) optical scanner may allow detection of the patient's head and/or face geometry and a program, e.g. a software, may guide and select a best fitting geometry. 3D printing and/or the selection from a number of sizes may provide the best interface to the patient's skin/surface. By using geometry data also the best fitting RF head coil may be selected as a modular component and both parts may be combined. Further, 3D printing may be used to build the complete respiratory mask using a predefined RF head coil geometry and/or printing of conductive tracks on a 3D shaped surface to allow a fully integrated design of the RF head coil and the respiratory mask. Further, in at least some embodiments, multi material 3D printing may also comprise forming a stiff basic mask, for example the mask body, by using a first material and then forming the interface, e.g. the seal or sealing portion, to the skin by using a second material, e.g. silicone. In at least some embodiments, additional features in the respiratory mask may be added by 3D printing, such as a window for additional e.g. camera based optical measurements or other sensor integration.

In at least some embodiments, the respiratory mask as a whole or one or more parts of it may be disposable.

Further, in at least some embodiments, the respiratory mask as a whole or one or more parts of it may be printable, particularly 3D printable, or may be printed on a flexible part or portion of the coil former. This coil former may act as a sealing, washer etc., which may preferably be biocompatible and may selectively be attached or removed from at least one further part or portion of the coil former.

In at least some embodiments, a fitting may be arranged between the coil and the sealing, and the fitting and/or the sealing may be disposable.

In an embodiment, the respiratory mask may be at least partly optically transparent.

Thus, the patient may be observed either directly or by use of an optical detecting means, such as camera etc., during MM scan. Further, the sedation status of the patient may be observed and/or controlled through optical detecting means.

According to an embodiment, the respiratory mask may comprise an indicator means, preferably a light guide, such as fiber or the like, adapted to be illuminated, adapted to optically indicate current delivery of gas, preferably a sedative, to the gas outlet.

The indicator means may also be referred to as a safety indicator which displays a current delivery status of e.g. a sedative or other medical gas. The indicator means may be illuminated in a first manner, e.g. a first color, to indicate a first delivery status, such as the non-feeding of gas, and may be illuminated in second manner, e.g. a second color, to indicate a second delivery status, such as the current feeding of gas. Additionally or alternatively, a breathing status of the patient may be indicated by the indicator means. The indicator means may, for example, be arranged on or in the respiratory mask.

In an embodiment, a fastening means adapted to fasten the first fastening portion and the second fastening portion together is selected from: a mechanical fastening means preferably adapted to be selectively released, an adhesive, etc.

Thus, the coil former and the respiratory mask may be separated from each other when needed, e.g. for cleaning etc.

According to an embodiment, the coil former and the respiratory mask may be integrally formed.

In other words, the coil former and the respiratory mask may be formed in one piece. Thus, the use of the RF head coil is simplified by fewer parts.

In an embodiment, the coil former may be manufactured by additive manufacturing.

Thus, the shape and/or size of the RF head coil may be adapted to the patient.

According to an embodiment, the coil former may be at least partly optically transparent.

Thus, the view of the patient is not obstructed and the patient may be optically monitored through the coil former.

In an embodiment, the coil former may comprise in a circumferential direction thereof related to the operable condition at least a first coil former portion and a second coil former portion, wherein at least one of the first coil portion and the second coil portion is optically transparent.

The one of the first coil former portion and the second coil former portion may be referred to as a base support adapted to support the patient's head from the back of the head and the other one of the first coil former portion and the second coil former portion may be referred to as a cover part adapted to cover the patient's head from the front of the head or the face. The first coil former portion and the second coil former portion may be attachable to each other. Preferably, the second coil portion may be optically transparent and may be adapted to comprise the respiratory mask. The RF head coil may be formed such that in the transparent field the RF head coil one or more conductors may be thin, flexible and/or lightweight. For example, capacitors may be omitted and one or more distributed wires may be molded in flexible transparent plastics. At least one of the first coil former portion and the second coil former portion may be flexible, wherein it may be preferred that the coil former portion forming a cover is flexible. Thus, the RF head coil may be further improved for MM.

According to an embodiment, at least one optical detection means, preferably one of a camera and an optical sensor, may be mounted on the coil former or the respiratory mask, wherein the at least one of the camera and the optical sensor camera may face the respiratory mask and/or the patient, preferably the patient's face, when the RF head coil is in the operable condition.

Thus, the sedation status of the patient may be optically determined and/or monitored and/or controlled. Further, motion of the patient may be monitored. This allows an anesthetist to remotely monitor the patient, and the anesthetist may sit close to the MR scanner instead to sit directly close to a bore. If In an embodiment, the respiratory mask and/or the RF head coil may comprise one or more optical markers adapted to be optically detected by an optical detection means. The optical markers may be arranged in pairs in such a way that a first optical marker, e.g. from the coil former, may be assigned to a second optical marker of e.g. the mask, or vice versa, and thus a correct positioning relative to the patient and/or a correct fixation of the fastening portions may be optically determined. In order to provide a guided positioning and/or fixing, the optical detection means may be adapted to provide a signal that may be used to generate instructions for a user, e.g. the patient, a clinician, technical assistant, etc., which may be used, for example, to guide the user from an actual position to a target position. Further, the optical markers may be used to detect motion of the patient.

According to an embodiment, at least one conductor may be arranged at least partially in or on the respiratory mask.

For example, a locally arranged coil conductor and/or an electronic preamplifier device may be located in or on the respiratory mask. This may allow an MR-based method to determine whether the respiratory mask is positioned correctly and/or, for example, to check if it is tight fit. For example, one or more conductor loops of the RF head coil may be arranged in or on the respiratory mask, e.g. embedded in its material. Preferably, the one or more loops may be arranged in the seal of the respiratory mask. This may also be beneficial in terms of general RF head coil design rules because it may maximize the loop cross section and may minimize the distance of the coil to the patient.

In an embodiment, the coil former may be at least sectionally flexible, and in the operable condition circumferentially free ends of the coil former may be connectable to each other through the respiratory mask fastened to each of the free ends. In at least some embodiments, the coils may at least partly printed on the flexible section of the coil former.

This allows the free ends of the coil former to be held together via the respiratory mask and the respiratory mask to be aligned towards the nose and/or mouth at the same time.

According to a second aspect, there is provided a magnetic resonance imaging system, MRI system. The MRI system comprises:
a bore,
a radio frequency head coil, RF head coil, comprising:
a coil former comprising at least a first leg and a second leg arranged at a distance from each other to define a space there between, the coil former having at least one first fastening portion arranged adjacent to the space, and
a respiratory mask comprising a gas outlet and at least one second fastening portion,
wherein in an operable condition in which the RF head coil is adapted to be arranged at least in sections around a head of a patient and in which the second fastening portion is adapted to be fastened to the first fastening portion, the gas outlet is disposed within the space.

The MM system may optionally be a part of a magnetic resonance, MR, guided radiotherapy system.

The RF head coil may be in accordance with one or more embodiments of the first aspect.

An effect of this MM system may be that the RF head coil and the respiratory mask are combined to one assembly. Thus, the functionalities of an RF head coil and a respiratory mask can be combined in one assembly, simplifying, for example, a patient's setup for e.g. MRI.

According to an embodiment, the MM system may further comprise a user guidance means adapted to support, by providing a user feedback, at least guided positioning of at least one of the respiratory mask and/or the RF head coil within the bore.

In this context, the user receiving the user feedback may be the patient himself, a clinician, a remote operator, etc. The user feedback may comprise one or more of an optical feedback, an acoustic feedback, or the like. The optical user feedback may comprise one or more of directional lights, an optical projection of directional indications, e.g. on an inner wall of the bore, etc. The acoustic user feedback may comprise direction announcements, or the like. Further, the guidance means may be adapted to support, by providing user feedback, guided fixation of at least one of the respiratory mask and/or the RF head coil within the bore. In particular, the user feedback may be one or more of an optical feedback, an acoustic feedback, etc., comprising, for example, directional indications to attach the respiratory mask to the RF head coil, etc.

In an embodiment, the user guidance means may further comprise at least one optical detection means, preferably at least one of a camera and an optical sensor, adapted to provide data on a current position of at least the respiratory mask and/or the RF head coil. The user guidance means may further be adapted to determine a relative position based on the provided current position and a desired target position, and to determine the user feedback indicating at least one of a direction and a distance to move from the detected or determined current position to arrive at the target position. To provide the user feedback the user guidance means may further comprise at least one of more of a display, directional lights, an optical projection means to project directional indications, e.g. on an inner wall of the bore, a speaker to provide acoustic user feedback, etc.

According to an embodiment, the MM system may further comprise a patient monitoring means adapted to detect at least one of (i) a sedation status of the patient and (ii) a motion of the patient based on at least a detected current position of the respiratory mask and/or the RF head coil relative to the patient or to another suitable reference point.

In an embodiment, the patient monitoring means may comprise at least one optical detection means, preferably one or more of a camera and an optical sensor, may be mounted on the coil former or the respiratory mask, wherein the at least one of the camera and the optical sensor camera may face the respiratory mask and/or the patient, preferably the patient's face, when the RF head coil is in the operable condition.

According to an embodiment, the sedation status optically detected by use of at least one of (i) at least one of a camera and an optical sensor mounted on the bore and facing the patient and (ii) at least one of a camera and an optical sensor mounted on the coil former or the respiratory mask.

In an embodiment, the sedation status may be detected by stimulating the patient with a gas supplied through the gas outlet.

For example, the respiratory mask, when not in a sedation delivery stage, may be fitted/actuated with an air jet delivery system that may be adapted to deliver air, e.g. cold, hot, bubble air, etc., to stimulate the patient response system to evaluate the patient sedation status. The bubble may also be used to create positive air pressure for breathing support or as a haptic feedback for breathing control.

According to an embodiment, the respiratory mask may be connected to an external system that may be controlled remotely or may be operated autonomously with in-built safety features. For example, during sedative delivery, the respiratory mask may be optically illuminated differently, using e.g. integrated fibre embedded to diffuse the light so that clear embarction can be created using sedation deliver as well as normal breathing stage. Further, during sedative delivery, fastening means of the of the respiratory mask may be tighted at least slightly so that sedation delivery volume can be controlled.

In an embodiment, the MRI system may further comprise a magnetic resonance, MR, image acquisition device. The MRI system may be adapted to detect, within one or more MR images taken by the MR image acquisition device, a conductor that may be arranged at least partially at the respiratory mask and to determine at least a current position of the conductor and/or the respiratory mask.

For example, at least one conductor loop of the RF coil may be arranged at, e.g. embedded in the seal of, the respiratory mask. For example as a part of an MR survey scan, an MR image may then be acquired in e.g. coronal orientation without any slice selection or with only selection of a thick slab covering the region of the respiratory mask (anterior-posterior co-ordinate may be calculated from the known position of the RF head coil). Only the seal conductor loop element may be used for signal reception of this image, and a small flip angle may be used for signal excitation. This may effectively provide a projection image containing a projection of the skin next to the seal onto a coronal plane. The resulting image may contain basically a bright line with the shape of the seal and noise everywhere else. If the mask is not properly fitted in some section of the seal, the respective signal will be reduced or even vanish in the projection image. The image may be analyzed automatically by suitable image processing methods, and in case staff or the patient may be asked to correct the position of the respiratory mask with automatic commands like: "Firmly attach the mask to the skin on its upper left side". Alternatively, proper fit of the respiratory mask may be checked manually by staff at the beginning of the MRI procedure. The above described projection image may be acquired afterwards as a first image of the MRI procedure. It may serve as a reference indicating tight fit of the respiratory mask. The acquisition may be repeated regularly during the imaging session, and the difference between the current and the reference image may be calculated. A difference may indicate that the fit is not tight anymore.

These and other aspects of the present invention will become apparent from and elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
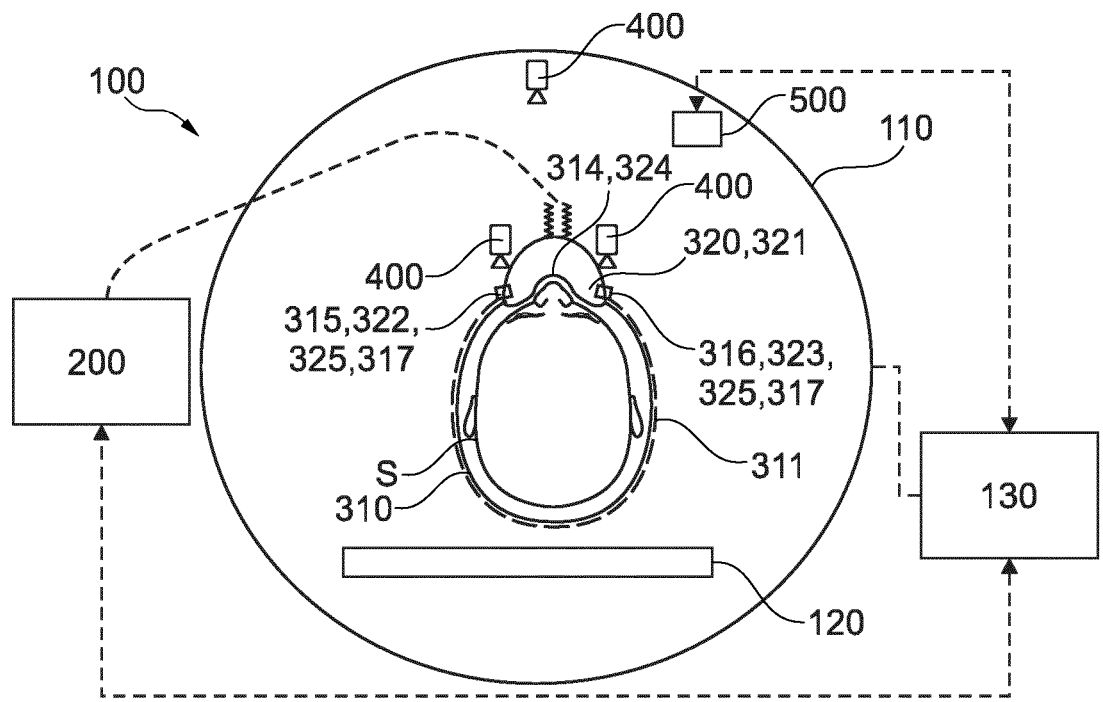
FIG. 1 shows in a schematic side view a magnetic resonance imaging system, MM system according to an embodiment.

FIG. 1 shows in a schematic side view a medical imaging system 100. In at least some embodiments, the system 100 may be operated based on magnetic resonance, MR, and may particularly be provided as a magnetic resonance imaging, MRI, system, which may optionally be a part of a magnetic resonance, MR, guided radiotherapy system.

The system 100 comprises an MR scanner with an MR bore 110, a patient support table 120, a control device 130 comprising at least a data processing device, an MR image acquisition device 140, a gas supply 200 adapted to store and dispense medical gas and a radio frequency head coil, RF head coil, 300.

According to FIG. 1, a patient S, which may be a human patient, is placed on top of the patient support table 120, which in an operable condition of the system 100 is arranged within the MR bore 110. Further in this operable condition, the RF head coil 300 is arranged at least in sections around a head of the patient S. The control device 130 is connected to the MR scanner and adapted to electronically control and/or monitor operation of the MR scanner and/or to receive signals, in particular image signals, from it. Further, the control device 130 is connected to the RF head coil 300 and adapted to electronically control and/or monitor operation of the RF head coil 300 and/or to receive signals from it and/or to transmit signals over it. Further, the control device 130 is connected to the gas supply 200 and adapted to electronically control and/or monitor operation of the gas supply 200.

The RF head coil 300 comprises a coil former 310, which may also be referred to as a housing or the like, and which may carry one or more coils 311, and which may optionally comprise one or more of conductors, loops, electric circuits, etc., so as to be adapted to at least detect MR signals etc. The coil former 310 comprises at least a first leg 312 and a second leg 313 arranged at a distance from each other to define a space 314 therebetween. Adjacent to the space 314, the coil former 310 comprises at least one first fastening portion 315, 316 arranged adjacent to the space 314. In at least some embodiments, the coil former 310 comprises at least one first fastening portion 315 arranged at the first leg 312 and at least a further first fastening portion 316 arranged at the second leg 313. In at least some embodiments, the coil former 310 may at least sectionally be flexible, which may be understood as e.g. elastic deformability, flexibility or the like. Further, in at least some embodiments, the coil former 310 may be at least partly optically transparent.

The RF head coil 300 further comprises a respiratory mask 320 which, at least in the operable condition of the RF head coil 300 and/or the system 100, is arranged or disposed within the space 314 formed between the first leg 312 and the second leg 313 of the coil former 310. Generally, the respiratory mask 320 may be provided as a CPAP mask, a sedation mask preferably adapted to supply a gaseous sedative, or the like. In the embodiment according to FIG. 1, the respiratory mask 320 is provided as a sedation mask. Accordingly, the gas supply 200 has stored a sedative to be dispensed to the patient S via the gas outlet 324 that is fluidically connected to the gas supply 200.

As illustrated in FIG. 1, the respiratory mask 320 is seated on the face of the patient S and covers both a nose and a mouth of the patient S, wherein another seat is conceivable, e.g. only on the nose or only on the mouth of the patient S. In at least some embodiments, the respiratory mask 320 may be at least semi-customized or fully customized and/or dedicated to the patient S. For example, the respiratory mask 320 may be manufactured by additive manufacturing, such as 3D printing. For this purpose, a 3D scanner may be used to scan and/or detect the patient's head and/or face geometry first. Then, based on the resulting geometry data, the best fitting respiratory mask 320 may be selected as a modular component or the respiratory mask 320 may be 3D printed. Also, multi-material 3D-printing may be used to e.g. combine the mask body 321 made from a first material with a seal of interface to the patient's skin made from a second material. Further, a window for additional e.g. camera based optical measurements or other sensor integration may be added.

The respiratory mask 320 comprises a mask body 321 which is dimensionally adapted to the patient's facial contour and comprises at least one second fastening portion 322, 323, disposed at the mask body 321 and adapted to be attached to the at least one first fastening portion 314, 315 of coil former 310. In the illustrated operable condition, one of the second fastening portions 322, 323 is fastened or attached to one of the first fastening portions 322, 323 and the other one of the second fastening portions 322, 323 is fastened or attached to the other one of the first fastening portions 315, 316. For example, mechanical fasteners, an adhesive or the like may be used for fastening. In this way, the respiratory mask 320 may be released from the coil former 310 to be cleaned etc. However, in at least some embodiments, the respiratory mask 320 may be integrated into the coil former 310 so as to form one piece with it. In this way, the coil former 310 and the respiratory mask 320 may be at least semi-customized for the patient S. It is noted that in the latter case the fastening between the coil former 310 and the respiratory mask 320 has not necessarily to be releasable.

Further, at the mask body 321, the respiratory mask 320 comprises a gas outlet 324 that opens into an inner side of the mask body 321 and that is adapted to be fluidically connected to the gas supply 200 as schematically illustrated in FIG. 1. In at least some embodiments, the fastening portions 322, 323 are arranged radially outside to the gas outlet 324. The respiratory mask 320 may be made from different materials, wherein, for example, the mask body 321 may be made from a rather rigid material and a seal adapted to be in contact with the skin or surface of the patient S may be made from a rather soft material, such as silicone or the like.

Still referring to FIG. 1, the system 100 may further comprise means to provide an at least semi-automated or fully-automated workflow management system, particularly adapted to guide a user for exact positioning and/or fixing of the coil former 310 and/or the respiratory mask 320, and/or adapted to monitor the patient S. Accordingly, in at least some embodiments, the system 100 comprises one or more of a user guidance means and a patient monitoring means. The user guidance means and/or patient monitoring means may at least partially implemented by the control device 130, i.e. in software and/or hardware, and may comprise common components which are described below.

As illustrated in FIG. 1, one or more optical detecting means 400 may be arranged within the bore 110. The optical detecting means 400 may be configured to optically detect the patient P and/or the RF head coil 300, and in particular the coil former 310 and/or the respiratory mask 320. Additionally or alternatively, the optical detecting means 400 may be arranged at the coil former 310 and/or the respiratory mask 320, as schematically indicated in FIG. 1. The optical detecting means 400 may comprise one or more cameras, optical sensors, or the like, and may be adapted to face the patient P and/or the coil former 310 and/or the respiratory mask 320. Further, the coil former 310 and/or the respiratory mask 320 may comprise one or more optical markers 317, 325 and/or sensors arranged so as to allow determining an actual or current position of the coil former 310 and/or the respiratory mask 320 by optically detecting it by use of the optical detecting means 400. For example, the optical markers 317, 325 and/or sensors may be arranged at the first fastening portion 315, 316 and/or the second fastening portion 322, 323, wherein relative positions of the first fastening portion 315, 316 and the second fastening portion 322, 323 to each other may be determined based on the optical detection. It is noted that the optical detecting means 400 is connected to the control device 130.

In at least some embodiments, the system 100 may further comprise one or more, preferably at least two, electromagnetic detector means and/or sensors. These electromagnetic sensors may be aligned to the respiratory mask 320, preferably, to perform a measurement from different positions in relation to each other. Further, the one or more electromagnetic sensor may be combined with the optical detecting means 400. The one or more electromagnetic detector means may be configured to perform a capacitive, inductive, or local resonator measurement. For example, a measurement result may comprise a distance and/or correct placement and/or alignment. This measurement result may be used in an autonomous imaging procedure or setup. The one or more measurement signals of the electromagnetic detector means may be processed, and if a respective signal level of at least two electromagnetic detector means is determined to be in a same value range or window, such as a voltage level or range, or the like, actions may be determined. For example, the system may provide instructions to the patient, e.g. an instruction to press the respiratory mask 320 against the face, etc. For example, if the respiratory mask 320 is not exactly positioned, the measurement signals of the two or more electromagnetic detector means may indicate a signal difference, and a feedback signal and/or alarm may generated and/or provided to the system, the patient, an remote operator, and/or an anesthetist, or the like.

Further, as illustrated in FIG. 1, one or more user feedback means 500, such as means adapted to provide an optical feedback, an acoustic feedback, etc., to the user, may be arranged within the bore 110 or at another suitable location. In this context, the user receiving the user feedback may be the patient himself, a clinician, a remote operator, etc. The user feedback may comprise one or more of an optical feedback, an acoustic feedback, or the like. The optical user feedback may comprise one or more optical output means, such as directional lights, an optical projection of directional indications, e.g. on an inner wall of the bore 110, etc. The acoustic user feedback may comprise direction announcements, or the like, which may be output using a speaker etc. It is noted that the user feedback means 500 is connected to the control device 130, and may be adapted to directly or indirectly interact with the optical detecting means 400.

Figure 2:
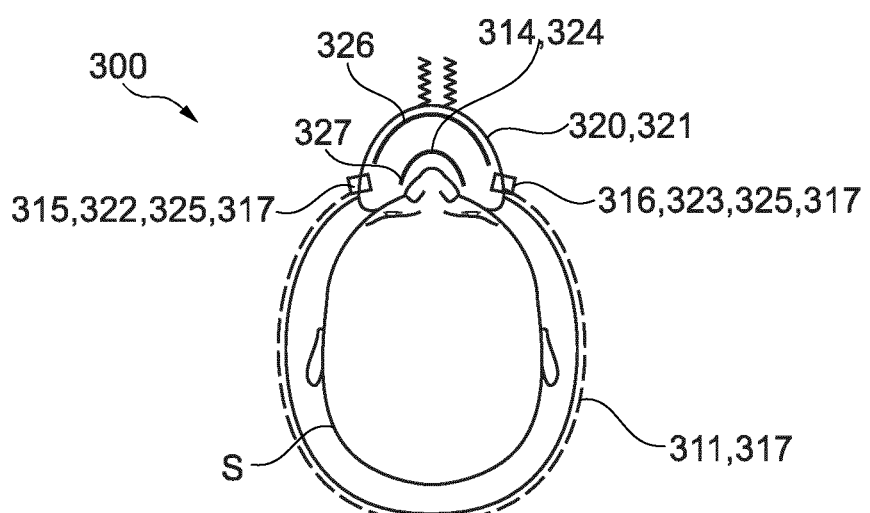
FIG. 2 shows in schematic top view a radio frequency head coil comprising a respiratory mask according to an embodiment.

FIG. 2 illustrates the RF head coil 300 according to an embodiment. At least in some embodiments, the respiratory mask 320 may further comprise one or more indicator means 326, such as a fiber adapted to be illuminated by light, adapted to optically indicate current delivery of gas to the gas outlet 324. For example, the indicator means 326 may be illuminated in a first color when gas is currently delivered and may be illuminated in another second color when no gas is currently delivered. The indicator means 326 may be connected to the control device 130.

In at least some embodiments, the coil former 310 may be at least sectionally flexible, and in the operable condition circumferentially free ends of the coil former 310 are connectable to each other through the respiratory mask 320 fastened to each of the free ends, as indicated in FIG. 2.

Still referring to FIG. 2, in at least some embodiments, at least one conductor 327 may be arranged at least partially in or on the respiratory mask 320. This conductor 327 may be detectable during MR imaging. The conductor 327 may be detectable by the MR image acquisition device 140 so as to determine a current position of the respiratory mask 320.

Figure 3:
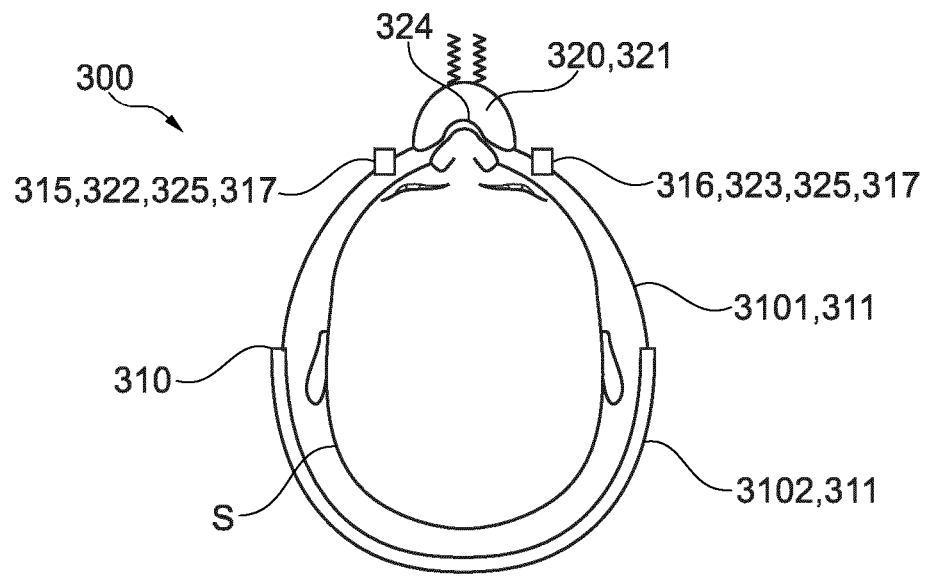
FIG. 3 shows in schematic top view a radio frequency head coil comprising a respiratory mask according to an embodiment.

FIG. 3 illustrates the RF head coil 300 according to an embodiment. In at least some embodiments, the coil former 310 may comprise in a circumferential direction thereof related to the operable condition at least a first coil former portion 3101 and a second coil former portion 3102, wherein at least one of the first coil former portion 3101 and the second coil former portion 3102 is optically transparent. The one of the first coil former portion 3101 and the second coil former portion 3102 may be referred to as a base support adapted to support the patient's head from the back of the head and the other one of the first coil portion 3101 and the second coil portion 3102 may be referred to as a cover part adapted to cover the patient's head from the front of the head or the face. The first coil former portion 3101 and the second coil former portion 3102 may be attachable to each other. The second coil portion 3102 may be optically transparent and may be adapted to comprise the respiratory mask 320, as indicated in FIG. 3. Further, at least one of the first coil former portion 3101 and the second coil former portion 3102 is flexible, as indicated in FIG. 3 by lines of varying thickness. By way of example, in the embodiment according to FIG. 3, the first coil former portion 3101 is flexible, whereas the second coil former portion 3102 is rigid. The coils 311 may partly be printed on the flexible first coil former portion 3101. The respiratory mask 320 may be arranged at the first coil former portion 3101. At least in some embodiments, the respiratory mask 320 may be e.g. printed, by additive manufacturing, on the flexible first coil former portion 3101.

Figure 4:
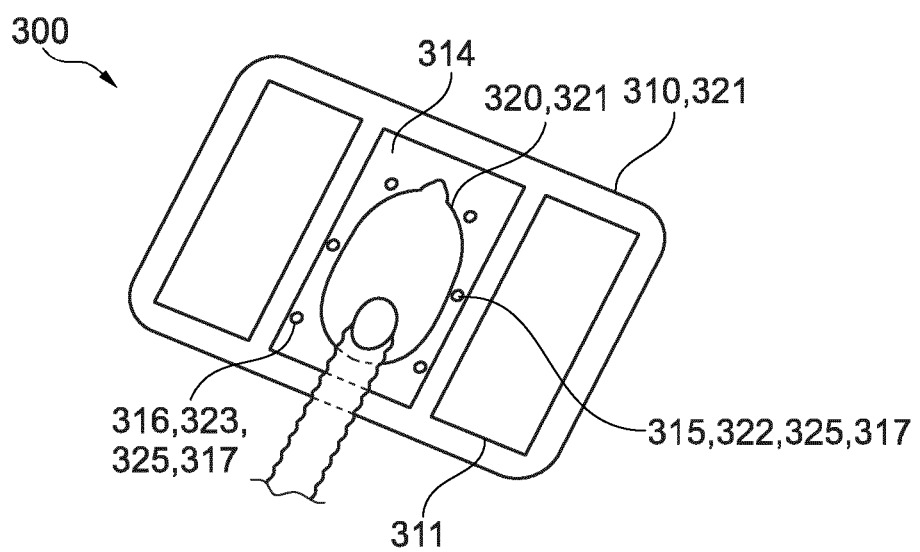
FIG. 4 shows in schematic top view a radio frequency head coil comprising a respiratory mask according to an embodiment.

FIG. 4 illustrates the RF head coil 300 according to an embodiment. It can be seen that the respiratory mask 320 is arranged in the space 314 between the first leg 312 and the second leg 313. In this embodiment, the respiratory mask 320 is formed separately to the coil former 310 and is attached to it. It is noted that the respiratory mask 320 may also be formed integrally as one piece with the coil former 310.

It has to be noted that embodiments of the invention are described with reference to different subject matters. In particular, some embodiments are described with reference to aerosol generator device claims whereas other embodiments are described with reference to the nebulizer system claims. However, a person skilled in the art will gather from the above and the following description that, unless otherwise notified, in addition to any combination of features belonging to one type of subject matter, also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

LIST OF REFERENCE SIGNS

100 medical imaging system
110 MR bore
120 patient support table
130 control device
140 MR image acquisition device
200 gas supply
300 RF head coil
310 coil former
3101 first coil former portion
3102 second coil former portion
311 coil
312 first leg
313 second leg
314 space
315 first fastening portion
316 first fastening portion
317 marker
320 respiratory mask
321 mask body
322 second fastening portion
323 second fastening portion
324 gas outlet
325 marker
326 indicator means
327 conductor
400 optical detecting means
500 user feedback means

The invention claimed is:

1. A radio frequency (RF) head coil for use in magnetic resonance imaging (MRI), the RF head coil comprising:
   a coil former comprising at least a first leg and a second leg arranged at a distance from each other to define a space therebetween, and having at least one first fastening portion arranged adjacent to the space, and
   a respiratory mask comprising a gas outlet and at least one second fastening portion,
   wherein in an operable condition in which the RF head coil is adapted to be arranged in sections around a head of a patient and in which the second fastening portion is adapted to be fastened to the first fastening portion, the gas outlet is disposed within the space,
   wherein the coil former is at least sectionally flexible.

2. The RF head coil according to claim 1, wherein the respiratory mask comprises:
   a mask body, dimensionally adapted to a patient's facial contour, and
   the at least one second fastening portion, disposed at the mask body and adapted to be attached to the at least one first fastening portion of the coil former,
   wherein the gas outlet opens into an inner side of the mask body and is adapted to be connected to a gas supply.

3. The RF head coil according to claim 1, wherein the respiratory mask is selected from: a continuous positive airway pressure (CPAP) mask, and a sedation mask, wherein the sedation mask is adapted to supply a gaseous sedative.

4. The RF head coil according to claim 1, wherein the respiratory mask is manufactured by additive manufacturing.

5. The RF head coil according to claim 1, wherein the respiratory mask comprises an indicator, wherein the indicator is adapted to optically indicate current delivery of gas to the gas outlet.

6. The RF head coil according to claim 1, comprising a fastener, wherein
   the fastener is adapted to fasten the first fastening portion and the second fastening portion together, wherein the fastener is selected from:
   an adhesive and a mechanical fastening element, wherein the mechanical fastening element is adapted to be selectively released.

7. The RF head coil according to claim 1, wherein the coil former is at least partly optically transparent.

8. The RF head coil according to claim 1, wherein
the coil former comprises in a circumferential direction thereof related to the operable condition at least a first coil former portion and a second coil former portion, wherein at least one of the first coil portion and the second coil portion is optically transparent.

9. The RF head coil according to claim 1, further comprising:
at least one optical detector mounted on the coil former and/or the respiratory mask,
wherein the at least one optical detector faces the respiratory mask and/or the patient when the RF head coil is in the operable condition.

10. The RF head coil according to claim 1, wherein
at least one conductor is arranged at least partially in or on the respiratory mask.

11. The RF head coil according to claim 1, wherein
in the operable condition circumferentially free ends of the coil former are connectable to each other through the respiratory mask fastened to each one of the free ends.

12. A magnetic resonance imaging system, MRI system, comprising:
a structure having a bore passing therethrough, and
the RF head coil of claim 1.

13. The MRI system according to claim 12, the MRI system further comprising:
a user guidance device adapted to support, by providing a user feedback, at least guided positioning of at least one of the respiratory mask and/or the RF head coil within the bore.

14. The MRI system according to claim 12, further comprising:
a patient monitor, wherein the patient monitor is adapted to detect at least one of:
(i) a sedation status of the patient; or
(ii) a motion of the patient based on at least a detected current position of the respiratory mask.

15. The MRI system according to claim 12, further comprising:
a magnetic resonance (MR) image acquisition device,
wherein the MRI system is adapted to detect, within one or more MR images taken by the MR image acquisition device, a conductor arranged at least partially at the respiratory mask and to determine at least a current position of the conductor and/or the respiratory mask.

16. A radio frequency (RF) head coil for use in magnetic resonance imaging (MRI), the RF head coil comprising:
a flexible coil former comprising at least a first leg and a second leg arranged at a distance from each other to define a space therebetween, and having at least one first fastening portion arranged adjacent to the space, and
a respiratory mask comprising a gas outlet and at least one second fastening portion,
wherein in an operable condition in which the RF head coil is adapted to be arranged around a head of a patient, and in which the second fastening portion is adapted to be fastened to the first fastening portion, the gas outlet is disposed within the space.

17. The RF head coil of claim 16, wherein the respiratory mask comprises:
a mask body, dimensionally adapted to a patient's facial contour, and
the at least one second fastening portion, disposed at the mask body and adapted to be attached to the at least one first fastening portion of the coil former,
wherein the gas outlet opens into an inner side of the mask body and is adapted to be connected to a gas supply.

18. The RF head coil of claim 16, wherein
the respiratory mask is selected from: a continuous positive airway pressure (CPAP) mask, and a sedation mask, wherein the sedation mask is adapted to supply a gaseous sedative.

19. The RF head coil of claim 16, wherein the respiratory mask comprises an indicator, wherein the indicator is adapted to optically indicate current delivery of gas to the gas outlet.

20. The RF head coil of claim 16, wherein the coil former is at least partly optically transparent.

* * * * *